United States Patent [19]
Thieme

[11] Patent Number: 6,008,056
[45] Date of Patent: Dec. 28, 1999

[54] SAMPLE VOLUME CONTROL FOR LATERAL FLOW CHROMATOGRAPHY

[75] Inventor: Thomas Thieme, Independence, Oreg.

[73] Assignee: Epitope, Inc., Beaverton, Oreg.

[21] Appl. No.: 08/864,758

[22] Filed: May 28, 1997

[51] Int. Cl.$^6$ .................................................. G01N 33/558
[52] U.S. Cl. .......................... 436/514; 422/55; 422/56; 422/57; 422/58; 435/287.1; 435/287.2; 435/287.7; 435/287.9; 435/805; 435/810; 435/970; 436/518; 436/530; 436/169; 436/805; 436/810
[58] Field of Search .................................. 422/55–58, 61; 435/287.1, 287.2, 287.7, 287.9, 805, 810, 970; 436/514, 518, 530, 169, 805, 810

[56] References Cited

U.S. PATENT DOCUMENTS

5,384,264   1/1995   Chen et al. ............................... 436/525

Primary Examiner—Christopher L. Chin
Attorney, Agent, or Firm—Townsend and Townsend and Crew LLP

[57] ABSTRACT

A method of assaying a preselected volume of sample on an chromatographic strip includes providing a sample receiving reservoir. This reservoir can receive a preselected volume of sample or a preselected volume of sample and reagent. The sample receiving reservoir has an overflow outlet. A moat is communicated to the overflow outlet of the sample receiving reservoir for receiving the sample or sample and reagent when the sample receiving reservoir is full. The mixed sample or sample and reagent fill the sample receiving reservoir, and discharge the excess sample through the overflow outlet to the moat. The sample receiving reservoir having the preselected volume of sample or sample and reagent is discharged on the chromatographic strip for assay. Provision is made for adding a density adding solute which is neutral to the chromatographic strip, the density adding solute occupying the sample receiving reservoir. As a consequence, dense sample first occupies the sample receiving reservoir with less dense excess sample being rejected.

26 Claims, 5 Drawing Sheets

SAMPLE VOLUME CONTROL FOR LATERAL FLOW CHROMATOGRAPHY

This invention pertains to the field of lateral trip chromatography. More particularly, this invention relates to the release of samples on lateral chromatographic strips where the volume of the sample released must be narrowly controlled.

BACKGROUND OF THE INVENTION

In REDUCTION OF FALSE POSITIVES IN ORAL-FLUID BASED IMMUNOASSAYS U.S. patent application Ser. No 08/806,245, filed Feb. 21, 1997, (owned by the same Assignee herein) there is disclosed the use of an immunochromatographic strip for testing oral fluids. In a preferred embodiment, the oral fluid or oral fluid/bile salt mixture can be pretreated by passage through a chelating matrix as it passes out of the oral fluid collection device (e.g., OraQuick®, Epitope, Inc., Beaverton, Oreg., USA) into the assay device (e.g., a rapid assay device such as the HIV1/2 Stat-Pak Ultra Fast HIV Assay, Chembio Diagnostic Systems, Medford, N.Y.).

In this test, and without the addition of the bile salts, it was found that mucopolysacchrides can interfere and give false positive results. It was discovered that by the addition of a bile salt, such as deoxycholate, that the false positives were reduced.

While the addition of the bile salts improved test results, these bile salts produced decreased incidence of false positives. It was found desirable to control the volume of sample released within narrower limits. Specifically, in a preferred embodiment, the bile salt is provided in an amount such that the final concentration of the bile salt in the oral fluid in the assay on the immuno-chromatographic strip ranges from about 0.1 weight percent to about 1 weight percent, more preferably from about 0.3 weight percent to about 0.6 weight percent, and most preferably from about 0.45 weight percent to about 0.55 weight percent of the solution applied to the assay. Naturally, the closer the approach of the sample to the preferred concentration, the better the overall test results.

As this example points out, the field of assaying with chromatographic strips often has needs for precise volume control. This is true, whether or not a reagent is present. Further, where a reagent is added, the reagent must be precisely controlled with respect to the volume of sample.

At the same time that precise volume control is required, it is desired that such tests be simplified to the greatest extent possible. Specifically, and because such tests are performed in large volume, it is not feasible to rely on clinical laboratory personnel to consistently meter the oral fluid relative to the provided chromatographic strip without error.

In the following description, it is to be understood that this invention will apply in any test where sample deposited on a chromatographic strip requires precise volume control. This precise volume control can be with or without pretreatment with a controlled volume of reagent, such as a salt.

It is to be understood that the chromatographic strip provides an environment that is unique as compared to many techniques looking for an analyte within a sample.

Considering the case of Daffern et al. U.S. Pat. No. 4,994,238, volume control occurs by an alternate method. In that disclosure testing for the analyte is performed on a reagent matrix layer. This reagent matrix layer has the capacity to absorb a defined volume only; by saturating the matrix layer the volume is controlled. Once the matrix layer is saturated, excess sample is allowed to overflow to a capturing absorbent layer.

The instant disclosure which follows is to be distinguished. Unlike the matrix layer with the defined volume, the chromatographic strip utilized here is not capable of self control of the volume utilized. Instead, and without volume control, the chromatographic strip here utilized can receive too little sample in which case the reagent is not properly apportioned with respect to the sample. Additionally, and where too little sample is used, the total sample and reagent may not adequately saturate the strip to give a correct indication of the analyte.

Alternately, too much sample can be delivered. In this latter case, reagent is supplied in insufficient quantity and sample is in excess quantity. Both deficiencies contribute to the likelihood of error.

SUMMARY OF THE INVENTION

A method of assaying a preselected volume of sample on an chromatographic strip includes providing a sample receiving reservoir. This reservoir can receive a preselected volume of sample or a preselected volume of sample and reagent. The sample receiving reservoir has an overflow outlet. A moat is communicated to the overflow outlet of the sample receiving reservoir for receiving the sample or sample and reagent when the sample receiving reservoir is full. The mixed sample or sample and reagent fill the sample receiving reservoir, and discharge the excess sample through the overflow outlet to the moat. The sample receiving reservoir having the preselected volume of sample or sample and reagent is discharged on the chromatographic strip for assay.

In a narrower embodiment, the apparatus and method of assaying a preselected volume of sample and a reagent on a chromatographic strip includes providing a conduit having an inlet for receiving sample, contained reagent within the conduit for mixing with the sample, and an outlet for discharging mixed reagent and sample. A sample collection pad saturated with sample to be tested is rapidly compressed over a short time period to discharge sample to the inlet of the conduit. The sample receiving reservoir is communicated to the outlet of the conduit for receiving the mixed sample and reagent flowing through the conduit. This sample receiving reservoir has a first bottom metering outlet and a second overflow outlet. A chromatographic strip is communicated to the first bottom metering outlet. A moat is communicated to the second overflow outlet for receiving sample when the sample receiving reservoir is full. Rapid compressing the sample collection pad over the short time period to rapidly discharge sample to the inlet of the conduit, causes release and mixing of the reagent to the sample, filling the sample receiving reservoir. When the reservoir is full, the reagent is depleted and the excess sample is diverted from the reservoir to the moat through the second overflow outlet. At the same time, the first bottom metering outlet discharges over a time period well exceeding the short time of sample containing pad compression. Thus, only the preselected volume of sample and reagent is supplied to the chromatographic strip to complete the assay.

DESCRIPTION OF THE PREFERRED EMBODIMENT

Figure 1:
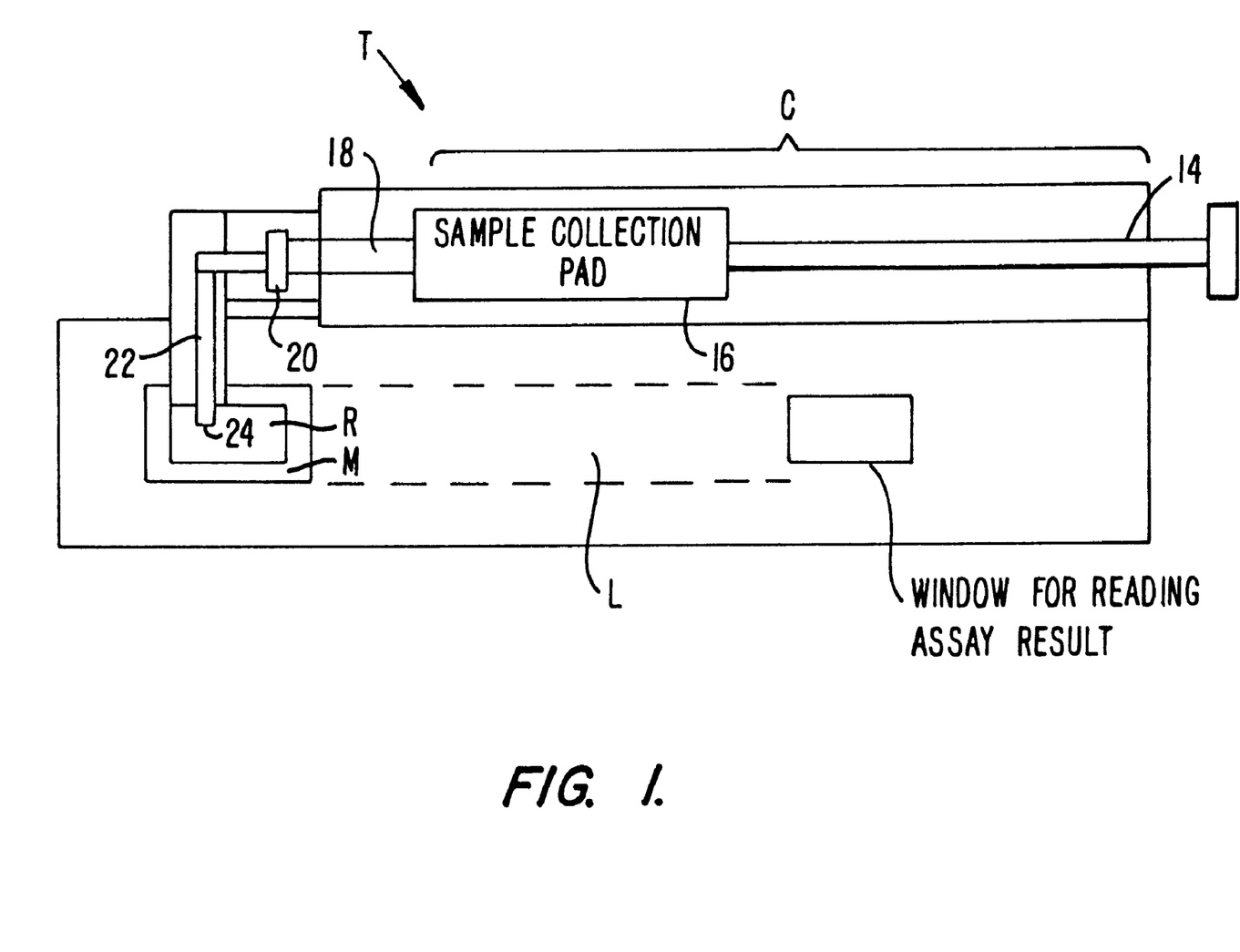
FIG. 1 is a block schematic of the sample pad compressor, sample treatment cartridge, sample reservoir, surrounding moat, and chromatographic strip.

Referring to FIG. 1, test apparatus T is shown having sample pad compressor C including plunger handle 14 which acts against sample collection pad 16. Compression of sample collection pad 16 by plunger handle 14 causes sample (and preservative) accumulated within sample collection pad 16 to be discharged to outlet 18 of sample pad compressor C. Typically, sample pad compressor C can be a modified syringe.

Sample pad compressor C discharges at outlet 18 to cartridge 20. Cartridge 20 can contain two solutes for introduction to sample discharged from sample collection pad 16. First, a density adding solute can be present. As will hereafter be made apparent, sample with a density adding solute preferentially occupies sample collecting reservoir R with dense sample for analysis; lighter excess sample is rejected from sample collecting reservoir R to moat M surrounding sample collecting reservoir R.

Second, lateral chromatographic strip L in many instances will require the presence of a reagent. This reagent can include a reporter labeled antigen or antibody for immunoassay. This being the case, cartridge 20 can contain this reagent.

Regardless of whether a density adding solute and/or a reagent are utilized, quantity of both in cartridge 20 will be controlled. Control will be to dissolve and mix with the volume of sample needed to fill sample collecting reservoir R when passing fluid to fill the reservoir passes through cartridge 20.

Sample passes from outlet 18 to conduit 22 and then into sample collecting reservoir R. Some attention can be devoted to the outlet into sample collecting reservoir R.

First, outlet 24 of conduit 22 discharges to the top of sample collecting reservoir R. This is to prevent mixing of sample within sample collecting reservoir R with excess sample.

Figure 2:
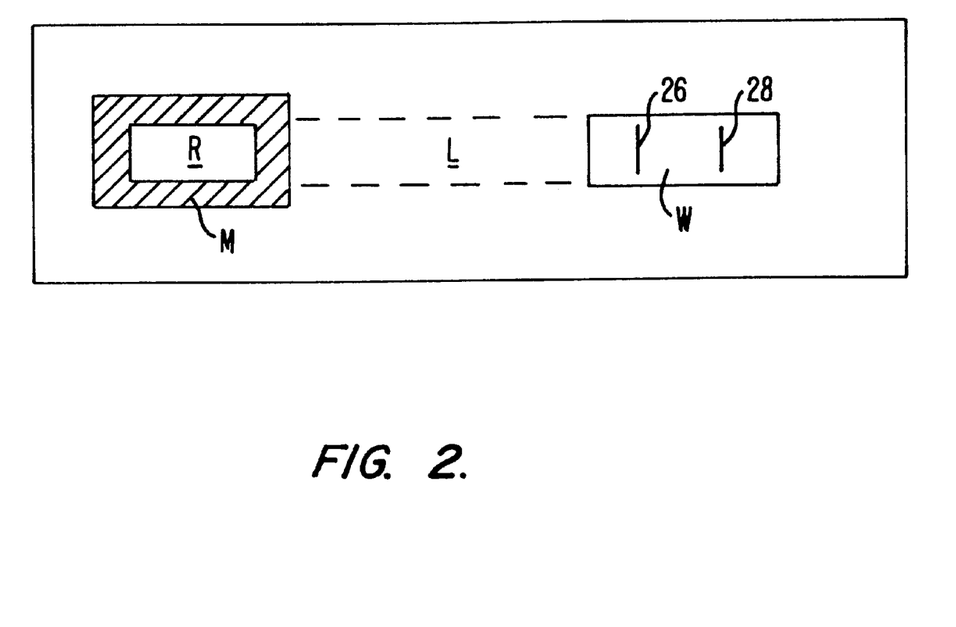
FIG. 2 is a view along lines 2—2 of FIG. 1 illustrating the moat, outlet port and surrounding moat; and, FIG. 3 is a view along lines 3—3 of FIG. 2 illustrating the profile of the retaining reservoir, the small metering aperture to the chromatographic strip, the overflow the surrounding moat, and the inlet port at the top of the reservoir; and, FIGS. 4A, 4B and 4C are respective diagrams of various embodiments of the process of this invention.

Second, sample collecting reservoir R is surrounded by moat M. Thus any additional sample—other than that sample necessary to fill sample collecting reservoir R—will cause the reservoir to overflow within moat M.

Figure 3:
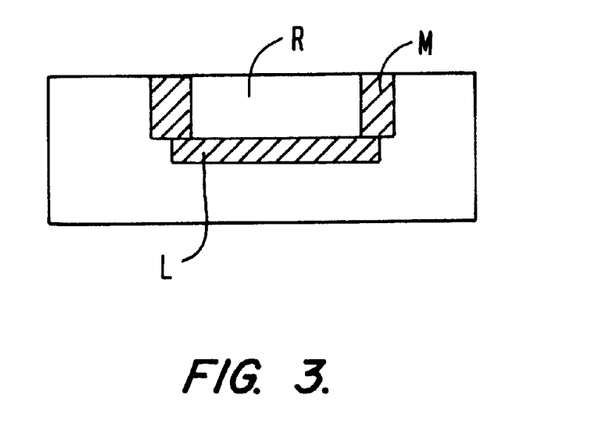

Once sample collecting reservoir R is full with sample, operation of the test can be understood with respect to FIG. 3. Specifically, sample collecting reservoir R has a bottom here defined by lateral chromatographic strip L. Remembering that sample pad compressor C rapidly discharges sample from sample collection pad 16, the reservoir will rapidly fill.

At the same time, lateral chromatographic strip L only absorbs sample (reagent and/or density adding solute) slowly. Specifically, lateral chromatographic strip L is selected to have a rate of absorption that is approximate 1/10th to 1/20th the rate at which sample is discharged from conduit 22 at outlet 24.

In typical immunoassays that use a particulate moiety as a detectable label, colored microparticles such as gelatin, dyed latex, or colloidal gold are labeled with a material (e.g. antibody) which binds the analyte of interest. The most common assay utilizing microparticle indicators is the lateral flow immunochromatography assay (see, e.g., U.S. Pat. No. 5,120,643, British Patent GB 2204398A, and European patent EP 0323605 B1).

In most lateral flow immunochromatography assays, microparticles are dried onto a sample application pad (typically glass fiber) which in turn is affixed to one end of a strip of chromatographic medium such as nitrocellulose. Another material binding to the analyte of interest is affixed to the chromatographic medium at or near the end opposite to the end having the application pad.

The liquid sample to be analyzed is placed on the pad, causing the suspension of the microparticles into the liquid and allowing any analyte in the liquid sample to bind to the analyte-binding material attached to the microparticles. The liquid sample leaves the application pad by diffusion and capillary action and begins to migrate along the nitrocellulose strip carrying the microparticles down the strip along with the liquid. When the liquid containing the suspended microparticles arrives at the region of the chromatographic strip bearing the second binding material, the analyte (if present in the original sample) will form a molecular bridge between the analyte-binding material on the microparticles and the analyte-binding material affixed to the strip, resulting in the immobilization of the microparticles at that point on the strip where the analyte-binding material is affixed. This immobilization of the microparticles results in a visible signal (e.g., a colored band or dot) at this point on the strip. If the analyte is not present in the sample, the microparticles will continue past this location on the chromatographic strip and a visible signal will not be produced.

It will be understood that it is not required for the practice of this invention that the lateral chromatographic assay be an immuno-chromatographic assay; it will be understood that this invention applies to all lateral chromatographic assays.

A review of lateral flow chromatographic assays can be found in Litman U.S. Pat. No. 4,391,904. In general, such a test involves the analyte in a sample, the binding agent, and reporter or signal generating liquid. The chromatographic support will general comprise a localized binding agent that will either directly capture the analyte or indirectly capture the analyte via an intermediate binding agent. Analytes include any biologic agent including proteins, antigens, hormones, small organic molecules, growth factors, and the like. Binding agents include antibodies, antigens, hormones, receptors, and any other biological molecule capable of specific recognition and binding.

The specific density adding solute for increasing the density of the sample is not critical so long as it does not interfere with necessary binding reactors. Such density agents include monosaccharide and polysaccharide (eg. disaccharides, trisaccharide, tetrasaccharide, etc.) such as glucose, sucrose and mammose and low molecular weight polymers such as ethylene glycol.

Finally, it will be understood that the rest of the test is conventional. Sample within sample collecting reservoir R conventionally transfers by migration along the length of lateral chromatographic strip L. Sample or sample and reagent sequentially interacts with mobile and immobile immunoreagents on the strip to produce a visible assay result at a distal position, usually test line 26. Since the quantity is precisely controlled at sample collecting reservoir R, sample will pass in due course first to test line 26 and then to control line 28. Control line 28 preferably contains immobilized antibody to human IgG or other universally present human serum component and will bind colored particles bearing such components from the sample. This control line will not show a positive result if an inadequate sample volume has been applied to the input port or the sample does not contain an adequate amount of human serum components. As described in REDUCTION OF FALSE POSITIVES IN ORAL-FLUID BASED IMMUNOASSAYS U.S. patent application Ser. No. 08/806,245 filed Feb. 21, 1997, analytes of interest in human oral fluid are often derived from the serum through mucosal transudation, and thus testing for a universal serum component in oral fluid provides sample adequacy information.

Figure 4A:
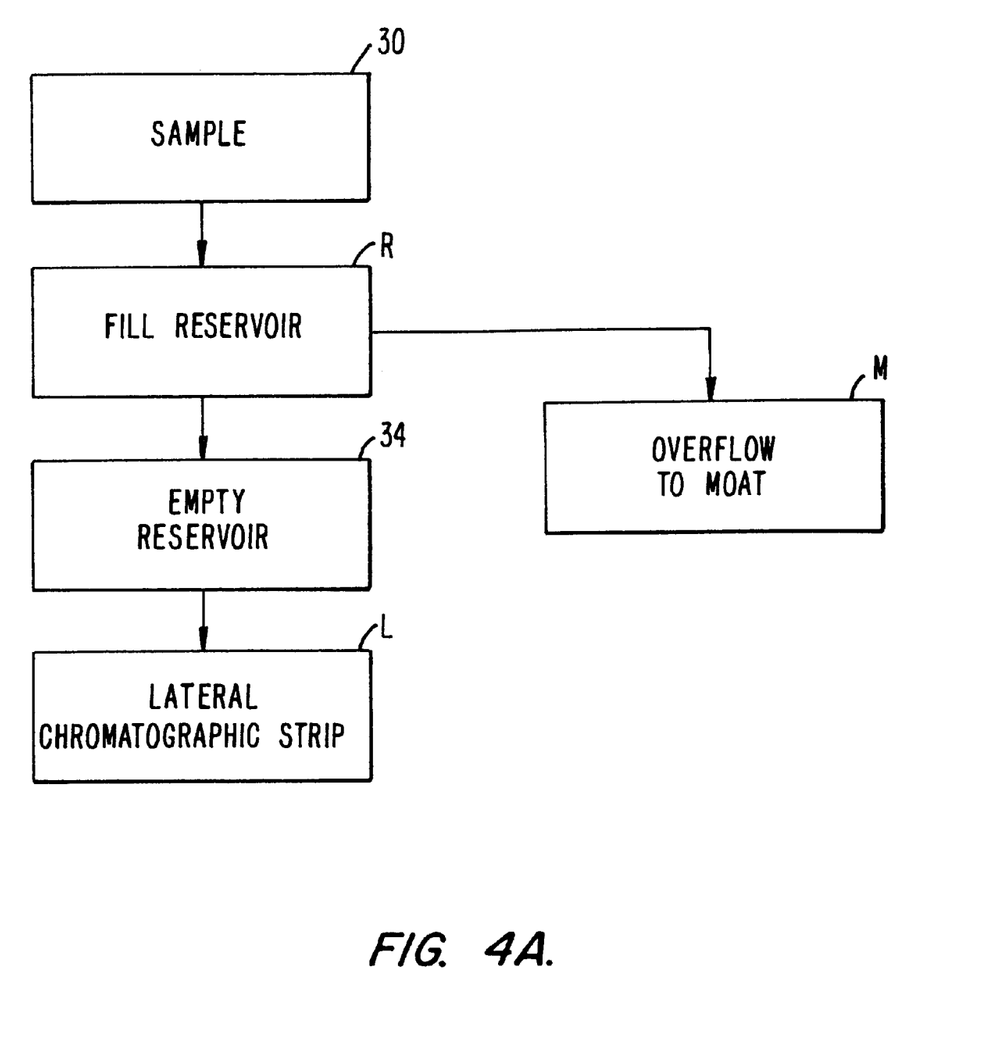

Referring to FIG. 4, a diagram of the process of this invention is easily understood. Specifically, sample 30 is discharged in sufficient quantity to fill sample collecting reservoir R. Overflow to moat M then occurs.

Thereafter, sample collecting reservoir R is emptied at emptying step 34 to lateral chromatographic strip L. I have shown the filling of sample collecting reservoir R to be carried out simultaneously with emptying step 34. This is not required. For example, plunger handle 14 could after crushing sample collection pad 16 upset sample collecting reservoir R so that only when the pad is completely crushed, would sample be discharged to lateral chromatographic strip L.

Figure 4B:
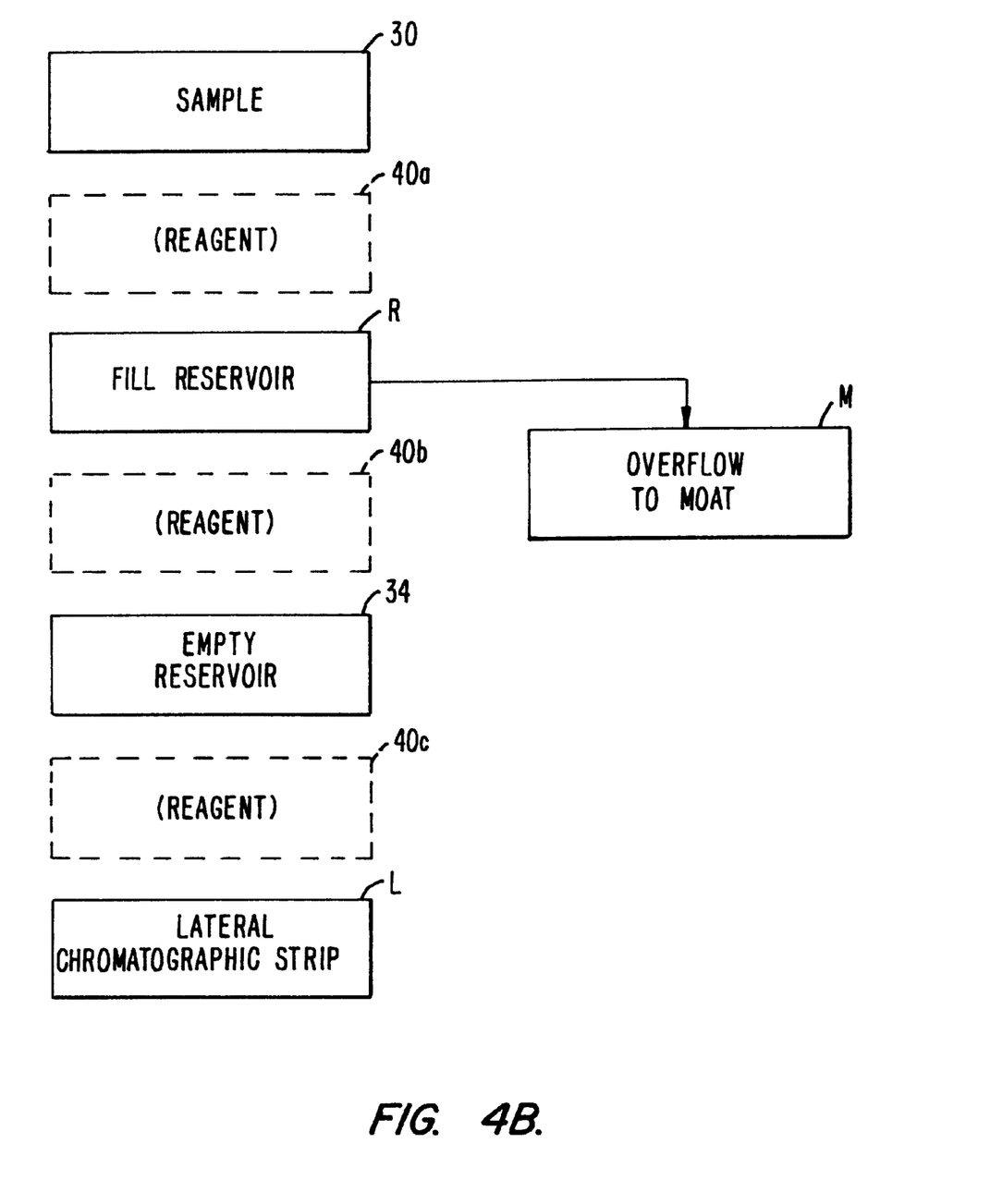

Referring to FIG. 4B, a diagram similar to FIG. 4A is shown, with the test here requiring that a reagent be added to the sample for an effective test at lateral chromatographic strip L. It should be clear that reagent adding step 40 can occur at the time that sample collection pad 16 is crushed to liberate the sample (see $40_a$) Alternately, reagent can be within sample collecting reservoir R and mix with the discharged sample at the reservoir (see $40_b$). Finally, reagent can be added to the sample when sample is placed onto lateral chromatographic strip L (see $40_c$).

Figure 4C:
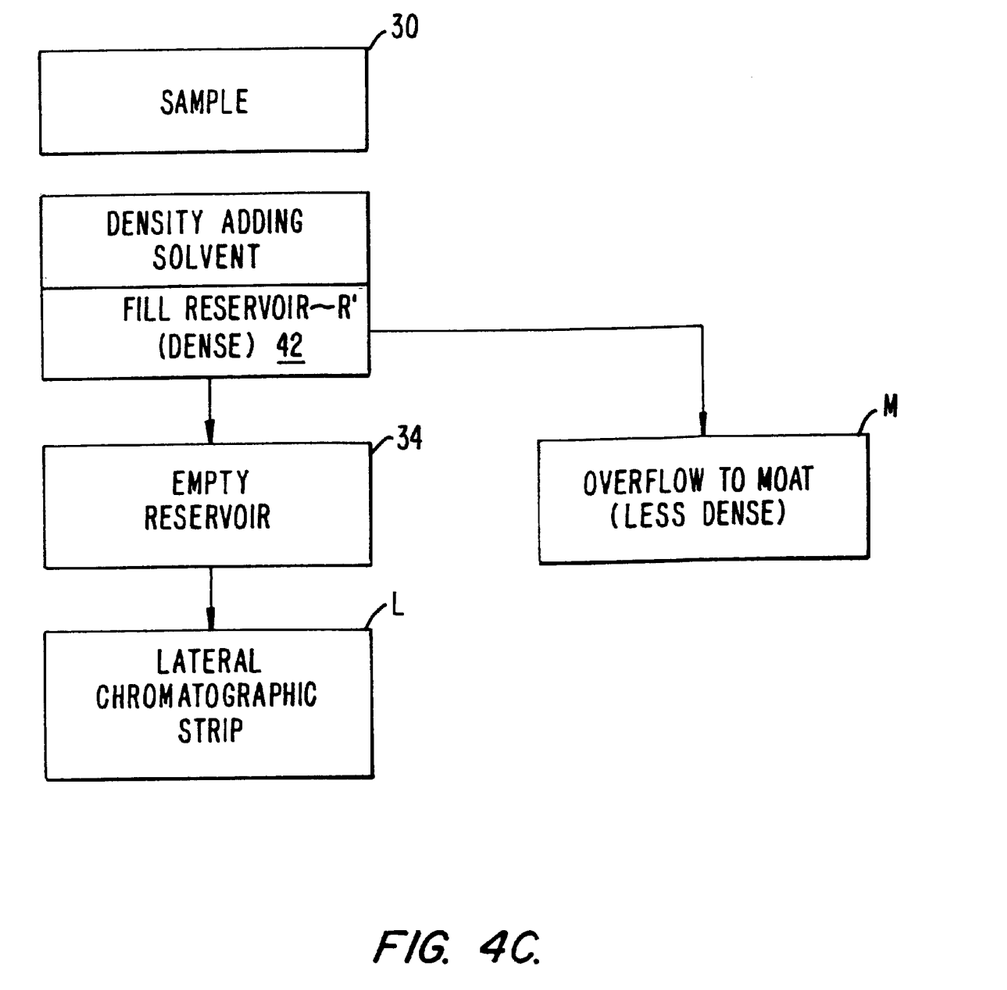

Finally, and with respect to FIG. 4C, a diagram of the process with the addition of density adding solute step 42 is illustrated. In this case, addition of density adding solute step 42 is shown. This density adding solute can be present in cartridge 20 or even in sample collecting reservoir R. This solute is preferably in sufficient quantity to add to the density of only that volume sufficient to fill sample collecting reservoir R. Thereafter, the density adding solute is depleted and overflow to moat M occurs only with excess sample having a reduced density. As a consequence, the likelihood of mixing in sample collecting reservoir R is reduced.

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to those of ordinary skill in the art in light of the teachings of this invention that certain changes and modifications may be made thereto without departing from the spirit or scope of the appended claims.

What is claimed is:

1. An apparatus for assaying a preselected volume of sample on a chromatographic strip comprising:

a sample receiving reservoir for receiving the preselected volume of sample;

an inlet for receiving sample to the sample receiving reservoir:

an overflow outlet for permitting sample in excess of the preselected volume of sample to overflow the sample receiving reservoir through the overflow outlet;

a chromatographic strip for receiving the preselected volume of sample in the sample receiving reservoir for assay on the chromatographic strip;

a moat in communication with the overflow outlet for receiving the sample when the sample receiving reservoir is full; and, means for discharging the sample to fill the sample receiving reservoir, and discharging excess sample through the overflow outlet to the moat.

2. An apparatus for assaying a preselected volume of sample on a chromatographic strip according to claim 1 and further comprising:

means for discharging the sample to fill the sample receiving reservoir, and discharging excess sample through the overflow outlet to the moat.

3. An apparatus for assaying a preselected volume of sample on a chromatographic strip according to claim 1 wherein the chromatographic strip is an immunochromatographic strip.

4. An apparatus for assaying a preselected volume of sample on a chromatographic strip according to claim 1 and further comprising:

means for mixing the sample and reagent to produce mixed sample and reagent before discharge to the chromatographic strip; and, a reagent for release to a preselected volume of sample to be assayed is placed between the inlet and the chromatographic strip.

5. An apparatus for assaying a preselected volume of sample on a chromatographic strip according to claim 1 and further comprising:

means for mixing the sample and density adding solute to produce mixed sample and density adding solute before discharge to the sample receiving reservoir; and, a density adding solute for release to a preselected volume of sample to be assayed is placed for release to the chromatographic strip between the inlet and the chromatographic strip.

6. An apparatus for assaying a preselected volume of sample on a chromatographic strip according to claim 1 and further comprising:

a conduit having an inlet for receiving the sample; an outlet for discharge to the sample receiving reservoir; and an interval for mixing sample therebetween; and;

the outlet for discharging the mixed sample through the conduit to the sample receiving reservoir.

7. An apparatus for assaying a preselected volume of sample on a chromatographic strip according to claim 6 and further comprising:

a reagent is placed between the inlet of the conduit and the chromatographic strip.

8. An apparatus for assaying a preselected volume of sample on a chromatographic strip according to claim 6 and further comprising:

reagent within the conduit is placed in a cartridge within the conduit.

9. An apparatus for assaying a preselected volume of sample on a chromatographic strip according to claim 1 and further comprising:

the sample receiving reservoir defines a bottom outlet;

the bottom outlet is communicating with the chromatographic strip for discharging the sample through the bottom outlet to the chromatographic strip.

10. An apparatus for assaying a preselected volume of sample on a chromatographic strip according to claim 1 and further comprising:

a sample collection pad for collecting a sample; and, means for compression of the pad when saturated with sample to discharge the sample.

11. An apparatus for assaying a preselected volume of sample on a chromatographic strip according to claim 1 and further comprising:

means for discharging the preselected volume of sample to the chromatographic strip for assay includes a sample receiving reservoir having a bottom metered outlet to the chromatographic strip.

12. An apparatus for assaying a sample on a chromatographic strip comprising:

a chamber for receiving a sample collection pad;

a cartridge having an inlet from the chamber and an outlet, the cartridge for containing a reagent for release to a preselected volume of sample to be tested;

a sample receiving reservoir in communication with the outlet of the cartridge for receiving the preselected volume of sample and reagent, the sample receiving reservoir having a first bottom and metering outlet and a second overflow outlet;

a chromatographic strip in communication with the first bottom and metering outlet for receiving the sample in the sample receiving reservoir for assay on the chromatographic strip;

a moat in communication with the second overflow outlet for receiving sample when the sample receiving reservoir is full; and, means for compressing the sample collection pad to discharge sample to fill the sample receiving reservoir, and discharge excess sample to the moat through the second overflow outlet whereby metered flow of the preselected volume is treated with reagent and metered to the chromatographic strip for assay.

13. An apparatus for assaying a sample on a chromatographic strip according to claim 12 comprising:

the chamber for receiving the pad with sample to be tested is a barrel of a sample pad compressor; and, means for compressing the sample collection pad is a plunger on the sample pad compressor.

14. A method of assaying a preselected volume of sample on a chromatographic strip comprising the steps of:

providing sample to be tested;

providing reagent to the sample being tested;

providing a sample receiving reservoir for receiving the preselected volume of sample;

providing an outlet from the sample receiving reservoir for overflow when the sample receiving reservoir receives sample in excess of the preselected volume of sample;

providing a chromatographic strip for receiving the preselected volume of sample in the sample receiving reservoir for assay on the chromatographic strip;

providing a moat communicated to the overflow outlet for receiving the sample when the sample receiving reservoir is full;

discharging the sample to fill the sample receiving reservoir, and discharging excess sample through the overflow outlet to the moat;

discharging the sample receiving reservoir having the preselected volume of sample to the chromatographic strip for assay;

detecting along the chromatographic strip for the presence of analyte; and, correlating for the presence or absence of the analyte.

15. A method of assaying a preselected volume of sample on a chromatographic strip according to claim 14 comprising the further steps of:

mixing the sample and reagent to produce mixed sample and reagent before discharge to the chromatographic strip.

16. A method of assaying a sample on a chromatographic strip according to claim 14 having the additional steps of:

providing a conduit having an inlet for receiving the sample and an outlet for discharge to the sample receiving reservoir; and, discharging the sample through the conduit to the sample receiving reservoir.

17. A method of assaying a sample on a chromatographic strip according to claim 16 wherein the step of:

providing a reagent between the inlet of the conduit and the chromatographic strip; and, mixing the sample and reagent before discharge to the chromatographic strip.

18. A method of assaying a sample on a chromatographic strip according to claim 17 wherein the step of:

placing reagent includes placing the reagent in a cartridge within the conduit.

19. A method of assaying a preselected volume of sample on a chromatographic strip according to claim 14 comprising the further steps of:

providing a density adding solute for release to a preselected volume of sample to be assayed;

mixing the sample and density adding solute to produce a mixture of higher density before discharge to the sample receiving reservoir.

20. A method of assaying a sample on a chromatographic strip according to claim 14 wherein:

providing the sample receiving reservoir with a bottom outlet;

communicating the bottom outlet to the chromatographic strip; and, discharging the sample through the bottom outlet to the chromatographic strip.

21. A method of assaying a sample on a chromatographic strip according to claim 20 wherein the step of:

discharging the preselected volume of sample to the chromatographic strip for assay includes providing a sample receiving reservoir with a metered outlet to the chromatographic strip.

22. A method of assaying a sample on a chromatographic strip according to claim 14 wherein the step of:

providing sample to be tested includes providing a sample collection pad saturated with sample and compressing the pad saturated with sample to discharge the sample.

23. A method of assaying a sample on a chromatographic strip according to claim 22 wherein the step of:

compressing the sample collection pad to discharge sample includes placing the sample collection pad within a sample pad compressor and compressing the sample discharge pad with the sample pad compressor.

24. A method of assaying a sample on a chromatographic strip according to claim 14 wherein the provided chromatographic strip is an immunochromatographic strip.

25. A method of assaying a sample on a chromatographic strip comprising the steps of:

providing a sample collection pad saturated with sample to be tested;

providing a cartridge containing a reagent for release to a preselected volume of sample to be assayed having an inlet for receiving sample and an outlet for discharging reagent treated sample;

providing a sample receiving reservoir in communication with the outlet of the cartridge for receiving the preselected volume of sample and reagent, the sample receiving reservoir having a first bottom and metering outlet and a second overflow outlet;

providing a chromatographic strip communication with the first bottom and metering outlet for receiving the sample and reagent in the sample receiving reservoir for assay on the chromatographic strip;

providing a moat in communication with the second overflow outlet for receiving sample when the sample receiving reservoir is full;

compressing the sample collection pad to discharge sample to the cartridge, fill the sample receiving reservoir, and discharge excess sample to the moat through the second overflow outlet whereby metered flow of the preselected volume is treated with reagent and metered to the chromatographic strip for assay;

detecting the presence of an analyte; and, correlating for the absence or presence of the analyte at the detecting step.

26. A method of assaying a sample on a chromatographic strip according to claim 25 comprising the further steps of:

placing the pad containing sample to be tested into a sample pad compressor having a plunger, and plunger housing, and an outlet; and the compressing step includes actuating the plunger to compress the pad containing sample to be tested within the sample pad compressor and discharging the sample pad compressor to the cartridge.

* * * * *